(12) United States Patent
Shimon (10) Patent No.: US 9,675,371 B2
(45) Date of Patent: Jun. 13, 2017

(54) DILATOR SHEATH SET

(71) Applicant: The Spectranetics Corporation, Colorado Springs, CO (US)

(72) Inventor: Jeffrey Shimon, Colorado Springs, CO (US)

(73) Assignee: The Spectranetics Corporation, Colorado Springs, CO (US)

( * ) Notice: Subject to any disclaimer, the term of this patent is extended or adjusted under 35 U.S.C. 154(b) by 381 days.

(21) Appl. No.: 14/195,692

(22) Filed: Mar. 3, 2014

(65) Prior Publication Data

US 2015/0245848 A1    Sep. 3, 2015

(51) Int. Cl.
| | |
|---|---|
| A61B 17/32 | (2006.01) |
| A61N 1/05 | (2006.01) |
| A61M 25/00 | (2006.01) |
| A61B 17/34 | (2006.01) |
| A61B 17/00 | (2006.01) |
| A61B 90/00 | (2016.01) |

(52) U.S. Cl.
CPC .......... *A61B 17/32* (2013.01); *A61B 17/3403* (2013.01); *A61M 25/0068* (2013.01); *A61N 1/056* (2013.01); *A61B 2017/00778* (2013.01); *A61B 2017/320044* (2013.01); *A61B 2090/062* (2016.02); *A61M 2025/0004* (2013.01); *A61M 2025/0008* (2013.01); *A61N 1/05* (2013.01)

(58) Field of Classification Search
CPC ................ A61B 17/32; A61B 17/3403; A61B 2017/00778; A61B 2017/320044; A61M 2025/0004; A61M 2025/0008
See application file for complete search history.

(56) References Cited

U.S. PATENT DOCUMENTS

| | | |
|---|---|---|
| D248,774 S | 8/1978 | Vallfors |
| 4,195,624 A | 4/1980 | Douglas |
| 4,449,532 A * | 5/1984 | Storz .................. A61B 1/00154 |
| | | 600/114 |
| 4,718,445 A | 1/1988 | Lundberg et al. |
| 4,862,891 A | 9/1989 | Smith |

(Continued)

FOREIGN PATENT DOCUMENTS

| | | |
|---|---|---|
| EP | 1267984 B1 | 11/2005 |
| EP | 1819390 B1 | 11/2009 |

(Continued)

OTHER PUBLICATIONS

International Search Report and Written Opinion issued in PCT/US2015/017514, mailed Jun. 19, 2015, 12 pages.

(Continued)

*Primary Examiner* — Julie A Szpira
(74) *Attorney, Agent, or Firm* — Faegre Baker Daniels LLP (57) ABSTRACT

This disclosure discusses various methods and devices for providing multiple types of indicators to be used with a sheath set. One type of indicator indicates the linear position and alignment of each of the sheaths within the sheath set, and another type of indicator indicates the rotational position and alignment of the sheaths. Both types of indicators may be included on the ends of the sheath set proximal to the user outside the patient's vasculature, thereby informing the user of the sheath set of the linear and rotational position and alignment of the ends of the inner and outer sheaths within the vasculature.

13 Claims, 2 Drawing Sheets

(56) References Cited

U.S. PATENT DOCUMENTS

| | | |
|---|---|---|
| 4,895,564 A | 1/1990 | Farrell |
| 5,011,478 A | 4/1991 | Cope |
| 5,011,482 A | 4/1991 | Goode et al. |
| 5,112,308 A | 5/1992 | Olsen et al. |
| 5,290,310 A | 3/1994 | Makower et al. |
| 5,292,311 A | 3/1994 | Cope |
| D355,255 S | 2/1995 | Chou |
| 5,431,639 A | 7/1995 | Shaw |
| 5,484,422 A | 1/1996 | Sloane, Jr. et al. |
| 5,499,975 A | 3/1996 | Cope et al. |
| 5,507,751 A | 4/1996 | Goode et al. |
| D373,827 S | 9/1996 | Polaniec |
| D377,526 S | 1/1997 | Mark |
| 5,632,749 A | 5/1997 | Goode et al. |
| 5,651,781 A | 7/1997 | Grace |
| D386,260 S | 11/1997 | Polaniec |
| 5,697,936 A | 12/1997 | Shipko et al. |
| 5,782,807 A * | 7/1998 | Falvai ............... A61M 25/0097 604/164.1 |
| D401,698 S | 11/1998 | Daniels |
| 5,980,515 A | 11/1999 | Tu |
| 6,010,520 A * | 1/2000 | Pattison ............... A61M 29/00 606/191 |
| 6,126,592 A | 10/2000 | Proch et al. |
| 6,189,574 B1 | 2/2001 | Iwasaki et al. |
| D438,629 S | 3/2001 | Stevens |
| D443,364 S | 6/2001 | Stevens |
| 6,613,002 B1 | 9/2003 | Clark et al. |
| 7,011,648 B2 | 3/2006 | Breskot et al. |
| D541,936 S | 5/2007 | Patterson |
| 7,435,214 B2 | 10/2008 | Kucklick et al. |
| D583,066 S | 12/2008 | Afifiyan et al. |
| 7,717,951 B2 | 5/2010 | Flagle et al. |
| D627,064 S | 11/2010 | Appelbaum et al. |
| D629,515 S | 12/2010 | Laurence |
| RE42,525 E | 7/2011 | Simonson |
| 8,066,730 B2 * | 11/2011 | Dorman ............... A61B 17/02 606/191 |
| 8,206,320 B2 | 6/2012 | Deal et al. |
| D665,076 S | 8/2012 | Sauer et al. |
| D666,712 S | 9/2012 | Laurence |
| 8,298,187 B2 | 10/2012 | Woodard et al. |
| 8,480,628 B2 | 7/2013 | Hawkins et al. |
| 8,535,293 B2 | 9/2013 | Faherty et al. |
| D727,527 S | 4/2015 | Tao |
| D731,075 S | 6/2015 | Staton et al. |
| 2004/0073088 A1 | 4/2004 | Friedman et al. |
| 2005/0070794 A1 | 3/2005 | Deal et al. |
| 2005/0137527 A1 | 6/2005 | Kunin |
| 2006/0235431 A1 | 10/2006 | Goode et al. |
| 2006/0247602 A1 | 11/2006 | Dulak et al. |
| 2007/0021768 A1 * | 1/2007 | Nance ............... A61M 25/0023 606/192 |
| 2007/0191708 A1 | 8/2007 | Gerold et al. |
| 2008/0154293 A1 | 6/2008 | Taylor |
| 2008/0154296 A1 * | 6/2008 | Taylor ............... A61B 1/32 606/190 |
| 2009/0143808 A1 * | 6/2009 | Houser ............... A61B 17/0057 606/170 |
| 2010/0063356 A1 | 3/2010 | Smith |
| 2011/0208284 A1 | 8/2011 | Hofmann et al. |
| 2012/0010471 A1 | 1/2012 | Mire et al. |
| 2012/0109177 A1 | 5/2012 | Ulmer |
| 2012/0116499 A1 | 5/2012 | Goetzen et al. |
| 2013/0090681 A1 | 4/2013 | Young et al. |
| 2013/0204342 A1 | 8/2013 | Kasprzak et al. |
| 2013/0261565 A1 | 10/2013 | Wong et al. |
| 2013/0317481 A1 | 11/2013 | Ellingwood et al. |
| 2014/0228874 A1 * | 8/2014 | Boyd ............... A61M 29/00 606/191 |
| 2014/0296974 A1 * | 10/2014 | Meyer-Brodnitz A61B 17/0218 623/2.11 |
| 2015/0099930 A1 | 4/2015 | Knapp |

FOREIGN PATENT DOCUMENTS

| | | |
|---|---|---|
| EP | 2089089 B1 | 8/2010 |
| EP | 2114319 B1 | 4/2011 |
| EP | 2626045 A1 | 8/2013 |
| WO | 2007067707 A1 | 6/2007 |

OTHER PUBLICATIONS

U.S. Appl. No. 29/483,813 entitled Sheath filed Mar. 3, 2014.
U.S. Appl. No. 29/483,815 entitled Sheath Set filed Mar. 3, 2014.
Byrd et al.; Intravascular Lead Extraction Using Locking Stylets and Sheaths; PACE, vol. 13, December, Part II 1990; pp. 1871-1875.
Byrd et al.; Intravascular Techniques for Extraction of Permanent Pacemaker Leads; The Journal of Thoracic and Cardiovascular Surgery, vol. 101, No. 6, Jun. 1991; pp. 989-997.
Byrd et al.; Lead Extraction —Indications and Techniques; Cardiology Clinics, vol. 10, No. 4, Nov. 1992; pp. 735-748.
Byrd Dilator Sheaths Telescoping Polypropylene; www.cookmedical.com; publication date unknown, accessed Apr. 28, 2014; Byrd Dilator Sheath available prior to filing date of present application.
International Preliminary Report on Patentability issued in PCT/US2015/017514, mailed Sep. 15, 2016, 8 pages.

* cited by examiner

DILATOR SHEATH SET

FIELD OF THE DISCLOSURE

The present disclosure relates generally to sheaths, including methods for using sheaths for separating tissue in a patient, and more specifically, to techniques for separating tissue attached to leads in a patient's vascular system.

BACKGROUND

Surgically implanted cardiac pacing systems, such as pacemakers and defibrillators, play an important role in the treatment of heart disease. In the 50 years since the first pacemaker was implanted, technology has improved dramatically, and these systems have saved or improved the quality of countless lives. Pacemakers treat slow heart rhythms by increasing the heart rate or by coordinating the heart's contraction for some heart failure patients. Implantable cardioverter-defibrillators stop dangerous rapid heart rhythms by delivering an electric shock.

Cardiac pacing systems typically include a timing device and a lead, which are placed inside the body of a patient. One part of the system is the pulse generator containing electric circuits and a battery, usually placed under the skin on the chest wall beneath the collarbone. To replace the battery, the pulse generator must be changed by a simple surgical procedure. Another part of the system includes the wires, or leads, which run between the pulse generator and the heart. In a pacemaker, these leads allow the device to increase the heart rate by delivering small timed bursts of electric energy to make the heart beat faster. In a defibrillator, the lead has special coils to allow the device to deliver a high-energy shock and convert potentially dangerous rapid rhythms (ventricular tachycardia or fibrillation) back to a normal rhythm. Additionally, the leads may transmit information about the heart's electrical activity to the pacemaker.

For both of these functions, leads must be in contact with heart tissue. Most leads pass through a vein under the collarbone, and the vein connects to the right side of the heart (right atrium and right ventricle). In some cases, a lead is inserted through a vein and guided into a heart chamber where it is attached with the heart. In other instances, a lead is attached to the outside of the heart. To remain attached to the heart muscle, most leads have a fixation mechanism, such as a small screw and/or hooks at the end.

Within a relatively short time after a lead is implanted into the body, the body's natural healing process forms scar tissue along the lead and possibly at its tip, thereby fastening it even more securely in the patient's body. Leads usually last longer than the batteries that power the device(s); so leads are simply reconnected to each new pulse generator (battery) at the time of replacement. Although leads are designed to be implanted permanently in the body, occasionally these leads must be removed, or extracted. Leads may be removed from patients for numerous reasons, including but not limited to, infections, lead age, lead malfunction, and lead obsolescence due to device upgrades.

Removal or extraction of the lead may be difficult. As mentioned above, the body's natural healing process forms scar tissue over and along the lead, and possibly at its tip, thereby encasing at least a portion of the lead and fastening it even more securely in the patient's body. In addition, the lead and/or tissue may become attached to the vasculature wall. Both results may, therefore, increase the difficulty of removing the leads from the patient's vasculature.

A variety of tools have been developed to make lead extraction safer and more successful. Current lead extraction techniques include mechanical traction, mechanical devices, and laser devices. Mechanical traction may be accomplished by inserting a locking stylet into the hollow portion of the lead and then pulling the lead to remove it. A mechanical device to extract leads may include a flexible tube called a sheath. One end of the sheath passes over the end of the lead outside of the body and enters the vasculature. This end of the sheath then advances over the lead and dilates, separates and/or cuts the surrounding tissue during advancement, while the other end of the sheath remains outside of the body. The end of the sheath that remains outside of the body is the end that is manipulated and controlled by the user. The mechanical device may include one sheath or a set of sheaths, such as an inner sheath and outer sheath which cooperate to separate the scar tissue from other scar tissue including the scar tissue surrounding the lead, and in some cases, the sheath(s) may also separate the tissue itself from the lead. Once the lead is separated from the surrounding tissue and/or the surrounding tissue is separated from the remaining scar tissue, the lead may be removed from the patient's vasculature using some other mechanical device(s), such as the mechanical traction device previously mentioned.

SUMMARY

There is a need for a device, method and/or system for a sheath set that includes indicators indicative of both the linear and rotational position of the sheaths with respect to one another that are visible to the user while the sheaths are in a patient's vasculature system.

Accordingly, the present disclosure discusses an indicator on an inner sheath at a linear position along the inner sheath's longitudinal axis such that when such indicator is aligned with the proximal end of the outer sheath, the user is informed that distal ends of the inner sheath and the outer sheath are linearly aligned such that the distal end of the inner sheath is located within the distal end of the outer sheath. The present disclosure also discusses that the inner sheath can have two halves, which are the mirror images of each, such that the distal end of the inner sheath can be removed from the outer sheath and the original proximal end can be inserted into the outer sheath such that when the same or additional indicator is linearly aligned with the now proximal end of the outer sheath, the user is informed that the now distal ends of the inner sheath and the outer sheath are linearly aligned such that the distal end of the inner sheath is located at and/or within the distal end of the outer sheath. Alternatively, the distal end of the outer sheath can be removed from the inner sheath and the original proximal end of the outer sheath can be inserted over the inner sheath such that when the same or additional indicator is linearly aligned with the now proximal end of the outer sheath, the user is informed that now distal ends of the inner sheath and the outer sheath are linearly aligned such that the distal end of the inner sheath is located at and/or within the distal end of the outer sheath.

The present disclosure also discusses having further indicators along the longitudinal axis of the inner sheath and outer sheath to indicate the rotational position of each of the inner sheath and outer sheath, as well as the rotational alignment of the inner sheath and with respect to the outer sheath. Providing both types of indicators—one type of indicator indicative of linear position and alignment and another type of indicator indicative of rotational position and alignment—on or towards the halves or ends of the inner sheath proximal to the user and/or outside the patient's vasculature, informs the user of the inner sheath of the linear and rotational positions and alignment of the inner sheath within the patient's vasculature. Also, providing an indicator indicative of rotational position and alignment of the outer sheath on or toward the proximal end of the outer sheath that is outside the patient's vasculature, informs the user of the outer sheath of the rotational position of the distal end of the outer sheath within the patient's vasculature. Providing the linear position indicator and rotational position indicator on the proximal end inner sheath in combination with providing the rotational position indicator on the proximal end of the outer sheath, informs the user of the sheath set of the linear position and alignment of the inner and outer sheaths relative to one another, the rotational position of each of the inner and outer sheaths, and the possible rotational alignment of the inner and outer sheaths relative to one another for the halves or ends of the inner sheath and outer sheath distal to the user and/or inside the patient's vasculature.

This linear and rotational position information is helpful to the user, particularly when the user is using the sheath set to navigate curved or tortuous paths of the patient's vasculature. Such information is also helpful to the user when the distal ends of the inner sheath and/or outer sheath are beveled such that the face of the distal end is angled, thereby creating two edges at the intersection of the face and the exterior surface of the outer sheath. In comparison to one another, one beveled edge (aka heel) is more proximal to the other beveled edge (aka tip), and one beveled edge (aka tip) is more distal to the other beveled edge (aka heel). Knowing the position of the proximal beveled edge and/or distal beveled edge of the inner sheath and/or outer sheath is helpful to the user when using the sheath set to navigate curved or tortuous paths of the patient's vasculature because the user may prefer to have the distal beveled edge(s) on the interior of the curved vasculature and the proximal beveled edge(s) on the exterior of the curved vasculature to reduce the likelihood of puncturing the vasculature as the sheath set passes therethough. Accordingly, it may be desirable for the indicators indicative of the rotational position of the inner sheath and outer sheath to be aligned with the proximal beveled edge(s) and/or distal beveled edge(s) along the longitudinal axes of the inner sheath and outer sheath.

A method of separating tissue surrounding a lead within a blood vessel, the method comprising the steps of: (a) inserting a sheath set over a proximal end of a lead within a blood vessel, the sheath set comprising: an outer sheath comprising a proximal end, a beveled distal end, a lumen between the proximal end and the beveled distal end, an exterior surface, and a longitudinal axis, wherein the beveled distal end forms a beveled proximal edge with the exterior surface of the outer sheath and a beveled distal edge with the exterior surface of the outer sheath, wherein the outer sheath further comprises a rotational position indicator on the exterior surface of the outer sheath and along the longitudinal axis of the outer sheath, wherein the rotational position indicator is aligned with the beveled distal edge; and an inner sheath comprising a first beveled end, a second beveled end, a center between the first beveled end and the second beveled end, an exterior surface, and a longitudinal axis, the inner sheath located at least partially within the lumen of the outer sheath, wherein the first beveled end forms a first proximal edge with the exterior surface of the inner sheath and a first distal edge with the exterior surface of the inner sheath, wherein the second beveled end forms a second proximal edge with the exterior surface of the inner sheath and a second distal edge with the exterior surface of the inner sheath, wherein the first proximal edge and the second proximal edge are proximate the center relative to the first distal edge and the second distal edge, respectively, wherein the inner sheath further comprises a rotational position indicator on the exterior surface of the inner sheath and along the longitudinal axis of the inner sheath, wherein the rotational position indicator is aligned with the first beveled distal edge and the second beveled distal edge, and a first indicator on the exterior surface of the inner sheath indicative, wherein the first indicator indicates the first beveled end of the inner sheath is aligned with the beveled distal end of the outer sheath when the first indicator is aligned with the proximal end of the outer sheath, and a second indicator on the exterior surface of the inner sheath, wherein the second indicator indicates the second beveled end of the inner sheath is aligned with the beveled distal end of the outer sheath when the second indicator is aligned with the proximal end of the outer sheath; (b) aligning the first indicator of the inner sheath with the proximal end of the outer sheath; (c) aligning the rotational position indicator of the inner sheath with the rotational position indicator of the outer sheath, thereby creating an aligned position for the inner sheath and outer sheath; (d) advancing the inner sheath and the outer sheath concurrently in the aligned position over the lead in the blood vessel; and (e) further advancing and rotating the inner sheath such that the first beveled end of the inner sheath extends distally of the beveled distal end of the outer sheath.

The method may also include the steps of retracting the inner sheath within the outer sheath to the aligned position, advancing the inner sheath and the outer sheath concurrently in the aligned position over the lead in the blood vessel, and further advancing and rotating the inner sheath such that the first beveled end of the inner sheath extends distally of the beveled distal end of the outer sheath. The method may further and/or alternatively include extending the outer sheath distally to the inner sheath, such that the inner sheath is refracted into the outer sheath.

A device, according to this disclosure, may include a sheath set for insertion into a blood vessel, the sheath set comprising: an outer sheath comprising a proximal end, a beveled distal end, a lumen between the proximal end and the beveled distal end, an exterior surface, and a longitudinal axis, wherein the beveled distal end forms a beveled proximal edge with the exterior surface of the outer sheath and a beveled distal edge with the exterior surface of the outer sheath, wherein the outer sheath further comprises a rotational position indicator on the exterior surface of the outer sheath and along the longitudinal axis of the outer sheath, wherein the rotational position indicator is aligned with the beveled distal edge; and an inner sheath comprising a first beveled end, a second beveled end, a center between the first beveled end and the second beveled end, an exterior surface, and a longitudinal axis, the inner sheath located at least partially within the lumen of the outer sheath, wherein the first beveled end forms a first proximal edge with the exterior surface of the inner sheath and a first distal edge with the exterior surface of the inner sheath, wherein the second beveled end forms a second proximal edge with the exterior surface of the inner sheath and a second distal edge with the exterior surface of the inner sheath, wherein the first proximal edge and the second proximal edge are proximate the center relative to the first distal edge and the second distal edge, respectively, wherein the inner sheath further comprises a rotational position indicator on the exterior surface of the inner sheath and along the longitudinal axis of the inner sheath, wherein the rotational position indicator is aligned with the first beveled distal edge and the second beveled distal edge, and a first indicator on the exterior surface of the inner sheath indicative of the first beveled end of the inner sheath being aligned with the beveled distal end of the outer sheath when the first indicator is aligned with the proximal end of the outer sheath, and a second indicator on the exterior surface of the inner sheath indicative of the second beveled end of the inner sheath being aligned with the beveled distal end of the outer sheath when the second indicator is aligned with the proximal end of the outer sheath.

A device, according to this disclosure, may also include a sheath set for insertion into a blood vessel, the sheath set comprising: an outer sheath comprising a proximal end, a beveled distal end, a lumen between the proximal end and the beveled distal end, an exterior surface, and a longitudinal axis, wherein the beveled distal end forms a beveled proximal edge with the exterior surface of the outer sheath and a beveled distal edge with the exterior surface of the outer sheath, wherein the outer sheath further comprises a rotational position indicator on the exterior surface of the outer sheath and along the longitudinal axis of the outer sheath, wherein the rotational position indicator is aligned with the beveled distal edge; and an inner sheath comprising a first beveled end, a second beveled end, a center between the first beveled end and the second beveled end, an exterior surface, and a longitudinal axis, the inner sheath located at least partially within the lumen of the outer sheath, wherein the first beveled end forms a first proximal edge with the exterior surface of the inner sheath and a first distal edge with the exterior surface of the inner sheath, wherein the second beveled end forms a second proximal edge with the exterior surface of the inner sheath and a second distal edge with the exterior surface of the inner sheath, wherein the first proximal edge and the second proximal edge are proximate the center relative to the first distal edge and the second distal edge, respectively, wherein the inner sheath further comprises a rotational position indicator on the exterior surface of the inner sheath and along the longitudinal axis of the inner sheath, wherein the rotational position indicator is aligned with the first beveled distal edge and the second beveled distal edge, and indicator on the exterior surface of the inner sheath and located at the center, wherein the indicator indicates the first beveled end of the inner sheath is aligned with the beveled distal end of the outer sheath when the indicator is aligned with the proximal end of the outer sheath, and wherein the indicator indicates the second beveled end of the inner sheath is aligned with the beveled distal end of the outer sheath when the indicator is aligned with the proximal end of the outer sheath.

The devices may further include an at least one pair of indicators comprising two markings having a space therebetween, wherein the space indicates the first beveled end of the inner sheath is aligned with the beveled distal end of the outer sheath when the proximal end of the outer sheath is aligned with the space. Also, the at least one pair of indicators may be aligned with the rotational position indicator on the exterior surface of the inner sheath.

A device, according to this disclosure, may also include a sheath comprising a first beveled end, a second beveled end, a center between the first beveled end and the second beveled end, an exterior surface, and a longitudinal axis, wherein the first beveled end forms a first proximal edge with the exterior surface of the inner sheath and a first distal edge with the exterior surface of the inner sheath, wherein the second beveled end forms a second proximal edge with the exterior surface of the inner sheath and a second distal edge with the exterior surface of the inner sheath, wherein the first proximal edge and the second proximal edge are proximate the center relative to the first distal edge and the second distal edge, respectively, wherein the inner sheath further comprises a rotational position indicator on the exterior surface of the inner sheath and along the longitudinal axis of the inner sheath, wherein the rotational position indicator is aligned with the first beveled distal edge and the second beveled distal edge, and a first indicator on the exterior surface of the inner sheath located a first predetermined distance from the first beveled end of the inner sheath, and a second indicator on the exterior surface of the inner sheath located a second predetermined distance from the second beveled end of the inner sheath, wherein the first predetermined distance and the second predetermined distance are either the same or different.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_a$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" may be used interchangeably herein. It is also to be noted that the terms "comprising", "including", and "having" may be used interchangeably.

A "catheter" is a tube that can be inserted into a body cavity, duct, lumen, or blood vessel, such as the vasculature system. In most uses, a catheter is a relatively thin, flexible tube ("soft" catheter), though in some uses, it may be a larger, solid, less flexible—but possibly still flexible—catheter ("hard" catheter). Additionally, the catheter may also have a working tip, such as a sharp blade to cut the bodily material (e.g., plaque) or a laser to ablate the bodily material, with which it contacts.

The term "indicator" as used herein is a distinguishing mark that provides an indication of position, direction and/or orientation. The indicator may be visual, non-visual or a combination thereof. An example of a visual indicator includes a printed mark perceptible to the human eye. An example of a non-visual indicator includes a tactile indicator, such as protrusion on and/or depression in a device such that the user of the device feels the indicator. Another example of a tactile indicator is an audible indicator perceptible to the human ear. A further type of non-visual indicator may include a radiopaque marker, which may require the use of visual aid equipment, such as that using ultrasound, x-ray, optical, magnetic, electro-magnetic, etc. technology. Other types of visual and/or non-visual indicators may include a mark that has light reflective optical property that differs from that of device associated with the mark, a magnet that creates a magnetic field, and a radio frequency parameter associated with the markers (which can be an active and/or passive Radio Frequency-Identification ("RFID") tag). The indicator may include one mark or a plurality of marks. Accordingly, the term "indicia" as used herein shall refer to a plurality of distinguishing marks that provide an indication of position, direction and/or orientation. An indicator of position can include relative position.

A "lead" as used herein is a conductive structure, typically an electrically insulated coiled wire. The electrically conductive material may be any conductive material, with metals and intermetallic alloys common. The outer sheath of insulated material is biocompatible and bio stable (e.g., non-dissolving in the body) and generally includes organic materials such as polyurethane and polyimide. Lead types include, by way of non-limiting example, epicardial and endocardial leads. Leads are commonly implanted into a body percutaneously or surgically.

The term "means" as used herein shall be given its broadest possible interpretation in accordance with 35 U.S.C. Section 112(f). Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

The term "sheath" as used herein shall mean a tubular structure, such as a catheter, having a lumen therethrough.

The term "sheath set" includes two or more sheaths, wherein one sheath is capable of being inserted within another sheath.

A "surgical implant" is a medical device manufactured to replace a missing biological structure, support, stimulate, or treat a damaged biological structure, or enhance, stimulate, or treat an existing biological structure. Medical implants are man-made devices, in contrast to a transplant, which is a transplanted biomedical tissue. In some cases implants contain electronics, including, without limitation, artificial pacemaker, defibrillator, electrodes, and cochlear implants. Some implants are bioactive, including, without limitation, subcutaneous drug delivery devices in the form of implantable pills or drug-eluting stents.

The term "tissue" as used herein shall mean an aggregate of similar cells forming a biological structural.

The term "vasculature" or "vascular system" as used herein shall mean a blood vessel or network of blood vessels within patient's circulatory system or any part thereof, including network of arteries, veins and capillaries that convey blood.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure may be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Figure 1:
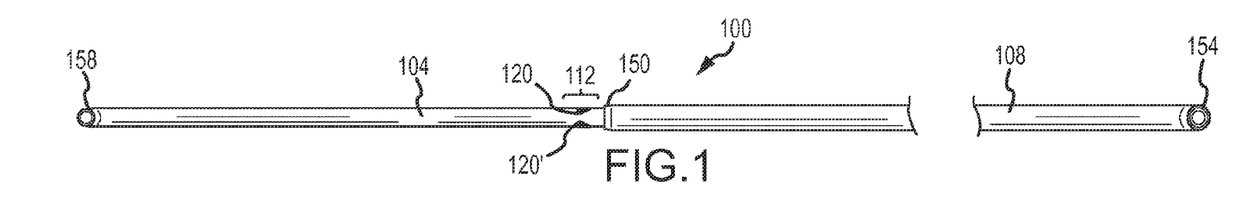
FIG. 1 is a top view of an embodiment of a sheath set including an inner sheath having one end disposed within an outer sheath and the other end of which is extending from the outer sheath.
Figure 2:
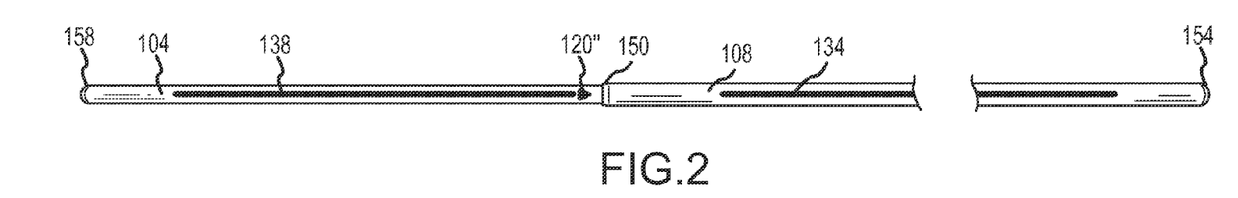
FIG. 2 is a bottom view of an embodiment of a sheath set including an inner sheath having one end disposed within an outer sheath and the other end of which is extending from the outer sheath.

With reference to FIG. 1 and FIG. 2, an exemplary sheath set 100 is depicted. The sheath set includes an inner sheath 104 and an outer sheath 108. Both the inner sheath 104 and the outer sheath 108 have two ends, a longitudinal axis, a lumen extending therethough along the longitudinal axis between the two ends, and an exterior surface. Depending upon the orientation of the inner sheath 104 and the outer sheath 108, the ends may be referred to as either a proximal end or a distal end. The proximal end generally refers to the end closest the user of the inner sheath 104 and the outer sheath 108, and the distal end generally refers to the end furthest from the user. In use, the proximal ends of the sheath set typically remain outside the patient's vasculature, and the distal ends of the sheath set typically enter the patient's vasculature.

The inner sheath 104 and the outer sheath 108 may preferably be constructed of a rigid and flexible biocompatible material, such as stainless steel or biocompatible polymers, using an extrusion process. An example of a biocompatible polymer is polypropylene. Additives, such as polyolefin elastomers, may also be combined with the polypropylene to obtain the desired rigidity, flexibility, fracture toughness and/or impact strength of the sheaths. Additionally, radiopaque material may further be added to the blend of biocompatible polymer. Adding the radiopaque material to the blend will allow a physician to see the inner sheath 104 and the outer sheath 108 within the patient's vasculature with the aid of visualization equipment, such as that is known in the art (e.g., fluoroscopy).

Figure 3:
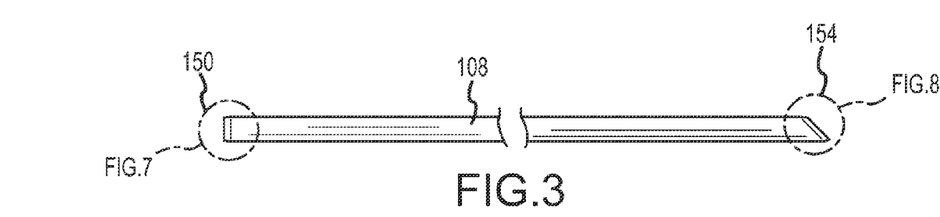
FIG. 3 is a side elevation view of an embodiment of an outer sheath.
Figure 7:
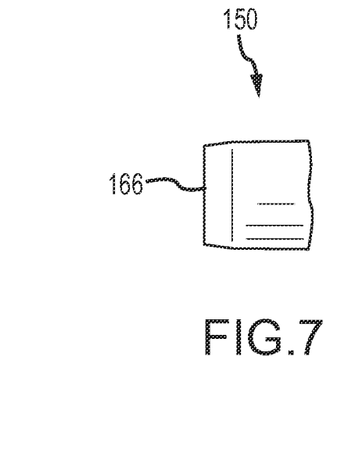
FIG. 7 is an enlarged view of one end of the outer sheath.

With reference to FIG. 3, there is depicted a side view of an exemplary outer sheath 108 having two ends 150, 154. The opposite side view of the outer sheath 108 is not shown. Nevertheless, it is a mirror image of FIG. 3. Referring to FIG. 7, there is depicted an enlarged view of end 150 of the outer sheath 108. The end 150 of the outer sheath 108 is tapered, and the face 166 of the end 150 of the outer sheath 108 is generally orthogonal to the longitudinal axis of the outer sheath 108.

Figure 8:
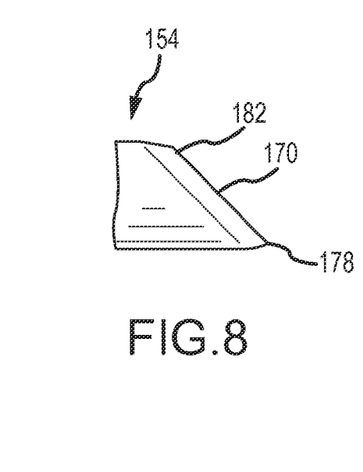
FIG. 8 is an enlarged view of one end of the outer sheath.

Referring to FIG. 8, there is depicted an enlarged view of end 154 of the outer sheath 108. Similar to end 150, the end 154 of the outer sheath 108 is tapered such that the thickness of the wall of the outer sheath 108 reduces towards the face 170. However, unlike the end 150, the face 170 of the end 154 is beveled with respect to the longitudinal axis of the outer sheath 108. Because the face 170 of the end 154 is beveled, the intersection of the face 170 and the exterior surface of the outer sheath 108 forms an acute angle, thereby creating an edge 178. Additionally, the intersection of the face 170 and the exterior surface of the outer sheath 108 forms an obtuse angle, thereby creating an edge 182. In comparison to the edge 182, the edge 178 is further distally of the center and of the end 150 of the outer sheath 108. That is, the edge 182 is located more proximal the center and the end 150 of the outer sheath 108 in comparison to the edge 178. Accordingly, the edge 182 may be referred to as a proximal edge, a beveled proximal edge, or a beveled proximal edge portion, and the edge 178 may be referred to as a distal edge, a beveled distal edge, or a beveled distal edge portion. That is, the distal edge 178 acts as a tip of the face 170, and proximal edge 182 acts as a heel of the face 170. Accordingly, distal edge 178 acts as a tip for the outer sheath 108. Furthermore, the use of the terminology for proximal edge and distal edge may be reversed in the event that the orientation of the outer sheath 108 is such that end 154 is located closer to the user than the end 150. Moreover, although FIGS. 3, 7 and 8 depict and discuss one orthogonally shaped end 150 and one beveled end 154, both ends of the outer sheath 108 may be orthogonal or both ends may be beveled.

Figure 5:
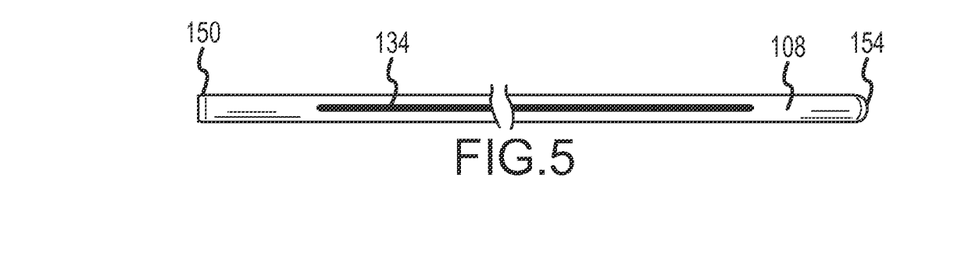
FIG. 5 is a bottom view of an embodiment of an outer sheath.

Referring to FIG. 5, there is depicted a bottom view of an exemplary outer sheath 108 having two ends 150, 154. This figure illustrates indicator 134 positioned along the longitudinal axis of the outer sheath 108. As discussed in more detail below, indicator 134 is used to determine the rotational position of the outer sheath 108 within a patient's vasculature, as well as the rotational alignment of the outer sheath 108 with respect to the inner sheath 104. The indicator 134 depicted in FIG. 5 is not only positioned along the longitudinal axis of the outer sheath 108, but the indicator 134 is also aligned with the edge 178 of the distal end 154 of the outer sheath 108. As discussed above with respect to FIG. 8, edge 178 is the most distal edge of the beveled face 170. Positioning indicator 134 in longitudinal alignment with the distal edge 178, informs the user (i.e., clinician) of the outer sheath 108 of the position of tip of end 154 located within the patient's vasculature because the indicator 134 is located on the outer sheath 108 at or towards the end 150 located proximal to the user and/or outside the patient's vasculature. This may be particularly helpful when the user is navigating the outer sheath 108, either alone or in conjunction with the inner sheath 104, through a curved or tortuous portion of the patient's vasculature. For example, assuming a portion of the vasculature is curved, there will be an interior segment and an exterior segment of the curved vasculature. And it may be desirable for the beveled distal edge 178 of the outer sheath 108 to pass through the curved portion of the vasculature along the interior segment rather than the exterior segment, thereby reducing the likelihood that the beveled distal edge 178 will rupture the vasculature as it passes therethrough. That is, it may be desirable for beveled proximal edge 182 of the outer sheath 108 to pass through the vasculature along the exterior curved segment and the beveled distal edge 178 of the outer sheath 108 to pass through the interior segment. If so, the user would navigate the outer sheath 108 with the indicator 134 aligned with the interior segment of the curved vascular portion. Accordingly, providing indicator 134 on the outer sheath 108 informs its user of the position of edge 178 of end 154 located within the patient's vasculature because the indicator 134, in addition to being located on the distal end of the outer sheath 108, is at, on, or towards the end 150 located proximal to the user and/or outside the patient's vasculature so that such indicator 134 is visible to the user during the procedure while the other distal end of the outer sheath 108 is located within patient's vasculature.

FIG. 5 depicts the indicator 134 in alignment with the distal beveled edge 178 of the end 154 of the outer sheath 108. However, the indicator 134 may alternatively be aligned with the proximal beveled edge 182 of the outer sheath 108. If so, positioning indicator 134 in alignment with the proximal beveled edge 182 of the distal end 154, informs the user (i.e., clinician) of the outer sheath 108 of the position of edge 182 of end 154 located within the patient's vasculature by looking at the indicator 134, which is also located on the outer sheath 108 at or towards the end 150 located proximal the user and/or outside the patient's vasculature. In such instance, it may be desirable for proximal edge 182 of the outer sheath 108 to pass through the vasculature along the exterior curved segment and the distal edge 178 of the outer sheath 108 to pass through the interior segment. If so, the user would navigate the outer sheath 108 with the indicator 134 aligned with the exterior segment of the curved vascular portion.

The indicator 134 in FIG. 5 is depicted as a solid line between the ends 150, 154 on the exterior surface of the outer sheath 108. However, the indicator may not be a solid line. For example, the indicator may alternatively include a series of broken lines, a series of dots, a series of lines and dots and/or a combination of lines, dots and other characters that are positioned in alignment with the longitudinal axis of the outer sheath 108 and/or in alignment with the proximal beveled edge 182 or distal beveled edge 178 of end 154. Additionally, the outer sheath may have multiple indicators aligned with the longitudinal axis of the outer sheath 108. For example, the outer sheath 108 may include one type of indicator positioned along its longitudinal axis that aligns with the proximal beveled edge 182 and another type of indicator positioned along its longitudinal axis that aligns with the distal beveled edge 178. Furthermore, the outer sheath 108 may include a third type of indicator positioned along its longitudinal axis that aligns with another reference point for the end 154. For example, the third type of indicator may indicate the mid-point of the face 170 of the end 154.

Figure 4:
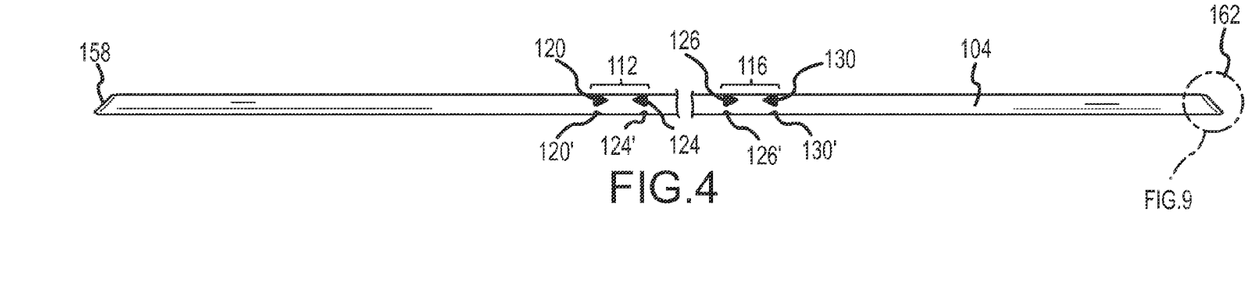
FIG. 4 is side elevation view of an embodiment of an inner sheath.
Figure 9:
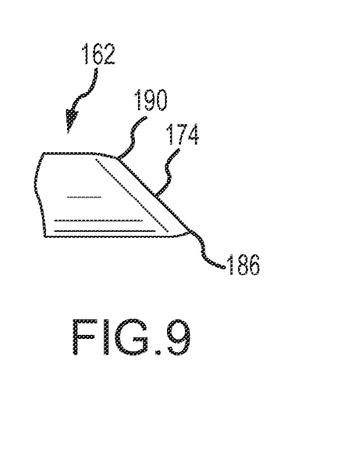
FIG. 9 is an enlarged view of one end of the inner sheath.

With reference to FIG. 4, there is depicted a side view of an exemplary inner sheath 104 having two ends 158, 162. The opposite side view of the inner sheath 104 is not shown. Nevertheless, it is a mirror image of FIG. 4. Referring to FIG. 9, there is depicted an enlarged view of end 162 of the inner sheath 104. Although only end 162 will be discussed, it shall be understood that end 158 may have the same configuration as end 162. The end 162 of the inner sheath 104 is tapered. The end 162 includes a face 174 that is beveled with respect to the longitudinal axis of the inner sheath 104. Because the face 174 of the end 162 is beveled, the intersection of the face 174 and the exterior surface of the inner sheath 104 forms an acute angle, thereby creating an edge 186. Additionally, the intersection of the face 174 and the exterior surface of the inner sheath 104 forms an obtuse angle, thereby creating an edge 190. In comparison to the edge 190, the edge 186 is further distally of the center and of the end 158 of the inner sheath 104. That is, the edge 190 is located more proximal the center and the end 158 of the inner sheath 104 in comparison to the edge 186. Accordingly, the edge 190 may be referred to as a proximal edge, a beveled proximal edge, or a beveled proximal edge portion, and the edge 186 may be referred to as a distal edge, a beveled distal edge, or a beveled distal edge portion. That is, the distal edge 186 acts as a tip of the face 174, and proximal edge 190 acts as a heel of the face 174. Accordingly, distal edge 186 acts as a tip for the inner sheath 104. Furthermore, the use of the terminology for proximal edge and distal edge may be reversed in the event that the orientation of the inner sheath 104 is such that end 162 is located closer to the user than the end 158. Moreover, although FIGS. 3 and 8 depict and discuss two beveled ends 158, 162, one or both ends of the inner sheath 104 may be orthogonally shaped.

Continuing to refer to FIG. 4, there are depicted two indicators, namely indicator 112 and indicator 116 on the exterior surface of the inner sheath 104. Indicator 112 and indicator 116 provide a user with an indication of the linear position and alignment of the inner sheath 104 with respect to the outer sheath 108. Specifically, when the inner sheath 104 is located within the lumen of the outer sheath 108 and indicator 112 on the inner sheath 104 is linearly aligned with the end 150 of the outer sheath 108, the indicator 112 indicates to the user that the end 162 of the inner sheath 104 is linearly aligned with the end 154 of the outer sheath 108. When the end 162 of the inner sheath 104 is linearly aligned with the end 154 of the outer sheath 108, the end 162 is located at the end 154 of the outer sheath, is within the outer sheath 134, and is not extending beyond the distal end 154 of the outer sheath 108. Additionally, when the inner sheath 104 is located within the lumen of the outer sheath 108 and indicator 112 on the inner sheath 104 is not linearly aligned with the end 150 of the outer sheath 108 such that the all of the indicator 112 is entirely visible to the user, then the indicator 112 indicates to the user that the end 162 of the inner sheath 104 is not linearly aligned with the end 154 of the outer sheath 108 and the end 162 of the inner sheath 104 is located proximally of the end 154 of the outer sheath 108 and potentially within the outer sheath 108. Furthermore, when the inner sheath 104 is located within the lumen of the outer sheath 108 and indicator 112 on the inner sheath 104 is not linearly aligned with the end 150 of the outer sheath 108 such that the entire indicator 112 is not at all visible to the user, then the indicator 112 indicates to the user that the end 162 of the inner sheath 104 is not linearly aligned with the end 154 of the outer sheath 108 and the end 162 of the inner sheath 104 is protruding beyond the end 154 of the outer sheath 108.

Similarly, when the inner sheath 104 is located within the lumen of the outer sheath 108 and indicator 116 on the inner sheath 104 is linearly aligned with the end 150 of the outer sheath 108, the indicator 116 indicates to the user that the end 158 of the inner sheath 104 is linearly aligned with the end 154 of the outer sheath 108. Indicators 112 and 116 on the exterior surface of the inner sheath 104 can also be linearly aligned with end 154 of the outer sheath 134 to indicate that the corresponding end 158 or 162 is linearly aligned with end 150 of the outer sheath 134.

Indicator 112 and indicator 116 may each include a single mark or a combination of marks. For example, FIG. 4 illustrates indicator 112 as a combination, particularly a pair of two triangular shaped marks 120, 124 spaced apart and facing one another such that the triangularly shaped marks 120, 124 are mirror images of one another because the apex of each triangularly shaped mark 120, 124 face each another. When the inner sheath 104 is located within the lumen of the outer sheath 108 and the space between the two apexes of the triangularly shaped marks 120, 124 is linearly aligned with the end 150 of the outer sheath 108, the indicator 112 indicates to the user that the end 162 of the inner sheath 104 is linearly aligned with the end 154 of the outer sheath 108. Similarly, FIG. 4 illustrates indicator 116 as a pair of two triangular shaped marks 126, 130 spaced apart and facing one another such that the triangularly shaped marks 126, 130 are mirror images of one another because the apex of each triangularly shaped mark 126, 130 face each another. When the inner sheath 104 is located within the lumen of the outer sheath 108 and the space between the two apexes of the triangularly shaped marks 126, 130 is linearly aligned with the end 150 of the outer sheath 108, the indicator 116 indicates to the user that the end 158 of the inner sheath 104 is linearly aligned with the end 154 of the outer sheath 108.

As illustrated in FIG. 2, the triangularly shaped mark 120" points toward the end 150 of the outer sheath 108. The shape, orientation and space between the triangularly shaped marks 120", 124" 126", 130", particularly the directional aspect of triangularly shaped mark and their spaced apart configuration, provide a user with an intuitive and useful indicator where to align inner sheath 104 with the outer sheath 108 such that ends 158, 162 of the inner sheath 104 linearly align with the end 154 of the outer sheath 108. However, other type of marks may be used as indicators 112, 116. The marks may have an alternate geometric shapes, such as a circle, oval, ellipse, crescent, curvilinear triangle, quatrefoil, parallelogram, square, rectangle, trapezoid, trapezium, rhombus, pentagon, hexagon, heptagon, octagon, nonagon, and decagon. The marks may also have other types of shapes or symbols, such as a kite, star, heart, cross, arrow, diamond, etc. Additionally, one indicator, such as indicator 112 may have a pair of marks with the same shape, and the other indicator, such as indicator 116 may have a pair of marks with the same shape but different than the shape of the marks for indicator 112. Furthermore, the indicator may include a combination of two differently shaped marks. Moreover, each mark may have the same color (e.g., red, orange, yellow, green, blue, purple, black, etc.) or a combination of different colors.

As mentioned above, the indicator 112, 116 may include a single mark rather than a combination of marks. For example, the indicators 112, 116 may include one of the shapes or symbols discussed above. Alternatively, the indicators 112, 116 may include an indicator, such as a line, stripe, bar, etc. Such indicator may have a single color (e.g., red, orange, yellow, green, blue, purple, black, etc.) or a combination of multiple colors. Furthermore, any of the indicators discussed above may have a particular color, and if multiple indicators are used, such indicator may have the same or different colors, thereby creating a color code therefor.

Figure 6:
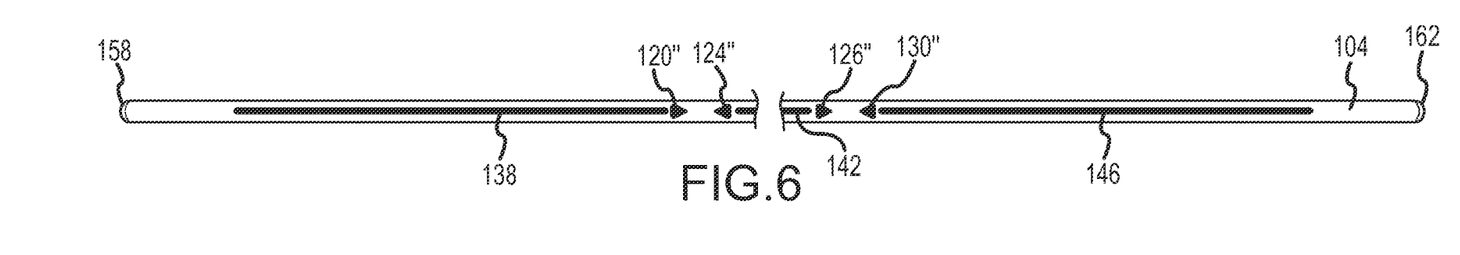
FIG. 6 is a bottom view of an embodiment of an inner sheath.

The indicators 112, 116 may include a set of multiple individual marks or multiple sets of marks around the circumference of the inner sheath 104 at the same linear position. Having a set of individual marks (e.g., any combination of 120, 120' and 120") or multiple sets of marks provide the user the ability to see the linear position of the inner sheath 104 with respect to the outer sheath 108 from multiple rotational perspectives. Referring to FIGS. 4 and 6, the indicator 112 may include three sets, wherein each set is a pair of triangularly shaped marks: (1) the first set includes a pair of triangularly shaped marks 120, 124; (2) the second set includes a pair of triangularly shaped marks 120', 124; and (3) the third set includes a pair of triangularly shaped marks 120", 124". Each set of marks may be spaced evenly around the circumference of the inner sheath 104 at the same linear distance from one of the ends 158, 162. For example, the first, second, and third set of marks may be spaced 120 degrees from each other around the circumference of the inner sheath 104. If a fourth set of marks was included as part of the indicator 112, the four sets of marks may be spaced 90 degrees from each other around the circumference of the inner sheath 104. Similarly, if a fifth set of marks was included as part of the indicator 112, the five sets of marks may be spaced 72 degrees from each other around the circumference of the inner sheath 104. Including multiple sets of marks, particularly three or more sets of marks, provides the user of the sheath set 100 with constant visualization of the linear orientation of the inner sheath 104 relative to the outer sheath. Although the majority of this paragraph discusses the indicator 112 and its corresponding sets of marks, it shall be understood that the same discussion applies to indicator 116 and its corresponding set of marks, wherein the first set includes triangularly shaped marks 126, 130; (2) the second set includes triangularly shaped marks 126', 130; and (3) the third set includes triangularly shaped marks 126", 130".

Referring to FIG. 6, there is depicted a bottom view of an exemplary inner sheath 104 having two ends 158, 162. This figure illustrates three indicators 138, 142, 146 positioned along the longitudinal axis of the inner sheath 104. As discussed in more detail below, the three indicators 138, 142, 146 are used to determine the rotational position of the inner sheath 104 within the patient's vasculature, as well as the rotational alignment of the inner sheath 104 with respect to the outer sheath 108. The three indicators 138, 142, 146 depicted in FIG. 6 are not only positioned along the longitudinal axis of the inner sheath 104, but the three indicators 138, 142, 146 are also aligned with the edge 186 of the beveled ends 158, 162 of the inner sheath 104. As discussed above with respect to FIG. 9, edge 186 is the most distal edge of the beveled face 174. Positioning indicators 138, 142, 146 in longitudinal alignment with the edge 186, informs the user (i.e., clinician) of the inner sheath 104 of the position of edge 186 for ends 158, 162 located within the patient's vasculature because the three indicators 138, 142, 146 are located on the inner sheath 104 at or towards one of the ends 158, 162 located proximal the user and/or outside the patient's vasculature. Accordingly, providing indicators 138, 142, 146 informs the user of the inner sheath 104 of the position of edge 186 of end 158, 162 located within the patient's vasculature because at least some of the indicators 138, 142, 146, in addition to being located on the distal end of the inner sheath 104, is at, on, or towards the opposite end 158, 162 located proximal to the user and/or outside the patient's vasculature so that such indicators 138, 142, 146 is visible to the user during the procedure while the other distal end of the outer sheath 108 is located within patient's vasculature.

As discussed above, with respect to the outer sheath 108, it may be helpful to the user when navigating the inner sheath 104, either alone or in conjunction with the outer sheath 108, through a curved or tortuous portion of the patient's vasculature to know where the distal edge 186 and proximal edge 190 are located with respect to the interior segment and the exterior segment of the curved vasculature. It may be desirable for the distal edge 186 of the inner sheath 104 to pass through the curved portion of the vasculature along the interior segment rather than the exterior segment, thereby reducing the likelihood that the distal beveled edge 186 will rupture the vasculature as it passes therethrough. That is, it may be desirable for proximal edge 190 of the inner sheath 104 to pass through the vasculature along the exterior curved segment and the distal edge 186 of the inner sheath 104 to pass through the interior segment. If so, the user would navigate the inner sheath 104 with the indicators 138, 142, 146 aligned with the interior segment of the curved vascular portion.

FIG. 6 depicts the indicators 138, 142, 146 in alignment with the distal beveled edge 186 of the ends 158, 162 of the inner sheath 104. However, one or all of the indicator 138, 142, 146 may alternatively be aligned with the proximal beveled edge 190 of the inner sheath 104. If so, positioning indicators 138, 142, 146 in alignment with the proximal beveled edge 190 of the ends 158, 162, informs the user (i.e., clinician) of the inner sheath 104 of the position of edge 190 of one of the ends 158, 162 located within the patient's vasculature by looking at one or more of the indicators 138, 142, 146, which are also located on the inner sheath 104 at or towards one of the ends 158, 162 located proximal the user and/or outside the patient's vasculature. In such instance, it may be desirable for proximal edge 190 of the inner sheath 104 to pass through the vasculature along the exterior curved segment and the distal edge 186 of the inner sheath 104 to pass through the interior segment. If so, the user would navigate the inner sheath 104 with the indicators 138, 142, 146 aligned with the exterior segment of the curved vascular portion.

The indicators 138, 142, 146 in FIG. 6 are depicted as a three solid lines between the ends 158, 162 on the exterior surface of the inner sheath 104, wherein the three lines are separated by indicators 112 and 116. However, each of the three indicators may not be a solid line. For example, one or more of the indicators may alternatively include a series of broken lines, a series of dots, a series of lines and dots and/or a combination of lines, dots and other characters that are positioned in alignment with the longitudinal axis of the inner sheath 104 and/or in alignment with the proximal beveled edge 190 or distal beveled edge 186 of ends 158, 162. Additionally, the outer sheath may have multiple indicators aligned with the longitudinal axis of the inner sheath 104. For example, the inner sheath 104 may include one type of indicator positioned along its longitudinal axis that aligns with the proximal beveled edge 190 and another type of indicator positioned along its longitudinal axis that aligns with the distal beveled edge 186. Furthermore, the inner sheath 104 may include a third type of indicator positioned along its longitudinal axis that aligns with another reference point for one of the ends 158, 162. For example, the third type of indicator may indicate the mid-point of the face 174 of one of the ends 158, 162.

It may also be preferable for the indicator 112, 116 and/or one set (or pair) of marks 120", 124", 126", 130" from each of the indicators 112, 116 on the inner sheath 104 to be aligned with the indicators 138, 142, 146 of the inner sheath 104. Aligning the indicator 112, 116 and/or one set (or pair) of marks 120", 124', 126", 130" with the indicator 138, 142, 146 on the inner sheath 104 in conjunction with the indicator 134 on the outer sheath 108 allows the user to quickly see the rotational position of the inner sheath 104, the possible rotational alignment of the inner sheath 104 and outer sheath 108, and the linear position of the inner sheath 104 with respect to the outer sheath 108. That is, the combination of indicators 112, 116 with at least one of the indicators 138, 142, 146 on the inner sheath 104 in conjunction with the indicator 134 on the outer sheath 108 allows the user to determine whether the distal ends 154, 162 (or 158) of the inner sheath 104 and outer sheath 108 are both linearly and rotationally aligned. This may be particularly helpful to the user of the sheath set 100 when navigating the sheath set 100 through a curved portion of the vasculature, as discussed above, so the user knows that the distal beveled edge of the inner and outer sheaths will pass along the interior portion of the curved vasculature, as opposed to the exterior curved portion.

Referring to the sheath set 100 depicted in FIG. 2, the sheath set includes a portion of the inner sheath 104 located within the outer sheath 108 such that the beveled distal end 162 (not shown) of the inner sheath 104 is linearly aligned with the distal end 154 of the outer sheath 108 as indicated by the alignment of indicator 112 (on the inner sheath 104) with the proximal end 150 of the outer sheath 108. Specifically, the proximal end 150 of the outer sheath 108 is located between the mark 120 and mark 124 of indicator 112 on the inner sheath, thereby indicating that the beveled distal end 162 of the inner sheath 104 is located within the outer sheath 108, is at the distal end 154 of the outer sheath, and is not extending beyond the distal end 154 of the outer sheath 108. Additionally, when the inner sheath 104 is located within the lumen of the outer sheath 108 and both marks 120 and 124 of indicator 112 on the inner sheath indicator 112 are visible to the user, then the indicator 112 indicates to the user that the end 162 of the inner sheath 104 is not linearly aligned with the end 154 of the outer sheath 108 and the end 162 of the inner sheath 104 is located proximally of the end 154 of the outer sheath 108 and potentially within the outer sheath 108. Furthermore, when the inner sheath 104 is located within the lumen of the outer sheath 108 and neither marks 120 nor 124 of indicator 112 on the inner sheath indicator 112 are visible to the user, then the indicator 112 indicates to the user that the end 162 of the inner sheath 104 is not linearly aligned with the end 154 of the outer sheath 108 and the end 162 of the inner sheath 104 is protruding beyond the end 154 of the outer sheath 108.

Continuing to refer to FIG. 2, the indicator 138 of the inner sheath 104 is also aligned with the indicator 134 of the outer sheath 108, thereby indicating that the distal beveled edge 186 of end 162 of the inner sheath 104 is rotationally aligned with the distal beveled edge 178 of end 154 of the outer sheath 108. That is, the beveled distal end 162 of the inner sheath 104 is both linearly and rotationally aligned with the beveled distal end 154 of the outer sheath 108, such that the beveled distal end 162 of the inner sheath 104 is located within the outer sheath and not extending beyond the distal end 154, and the distal beveled edge 186 of end 162 of the inner sheath 104 is rotationally aligned with the distal beveled edge 178 of end 154 of the outer sheath 108.

Knowing the linear and rotational orientation of the inner sheath 104 and outer sheath with respect to one another, a user may advance the sheath set 100 in this aligned configuration over a lead and insert sheath set 100 into a patient's vasculature to separate tissue surrounding the lead. That is, the user may concurrently advance the inner sheath 104 and outer sheath 108 over the end of the lead outside of the patient and into the patient's vasculature in such aligned position. Once the sheath set 100 contacts the tissue, the user may rotate and/or advance the inner sheath 104 beyond the distal end 154 of the outer sheath 108 to separate tissue surrounding the lead using the face 174 and/or edges 186, 190 of the beveled distal end 162. The beveled distal end 162 of the inner sheath 104 may be retracted back into the outer sheath 108 by the user, and potentially realign the inner and outer sheaths, such that the sheath set 100 is further advanced in unison over the lead and deeper into the vasculature. The user may then again rotate and/or advance the inner sheath 104 beyond the distal end 154 of the outer sheath 108 to create additional separation of the tissue surrounding the lead using the face 174 and/or edges 186, 190 of the beveled distal end 162. This process of concurrently advancing, in unison, the inner sheath 104 and outer sheath 108 over the lead and into the patient's vasculature in such aligned position, then rotating and/or advance the inner sheath 104 beyond the distal end 154 of the outer sheath 108, and followed by retraction of the inner sheath 104 into the outer sheath 108 may be repeated until the desired amount of tissue has been separated from the lead. The outer sheath 108 can also be advanced in front of the inner sheath 104 to aid in separation of lead from tissue; for example, when the tissue is directly attached to the lead, it is possibly more difficult to dilate than tissue radially positioned around the lead but unattached to the lead. Accordingly, it may be advantageous to advance either end 150 or end 154 or both ends into the tissue and initiate dilation prior to introducing either end 158 or end 162 of the inner sheath to completing the dilation of the tissue surrounding and/or attached to the lead.

As discussed above, when navigating the sheath set 100 through a curved portion of a patient's vasculature, it may be desirable for the beveled distal edge 186 of the inner sheath 104 and the beveled distal edge 178 of the outer sheath to pass through the vasculature along the interior curved segment and the beveled proximal edge 190 of the inner sheath 104 and the beveled distal edge 182 of the outer sheath to pass through the vasculature along the exterior curved segment. And the indicator of the present disclosure allow the user to know the linear and rotational alignment of the inner sheath 104 and the outer sheath 108 as the sheath set advances through the vasculature, thereby minimizing the likelihood of rupturing the vasculature, particularly as the sheath set 100 advances through a curved section of the vasculature.

A number of variations and modifications of the disclosure may be used. For example, the end 158 of the inner sheath 104 may be inserted into the outer sheath 108 and aligned with its end 154. If so, the indicator 116, along with its marks 126, 126', 126", 130, 130', and 130", on the inner sheath 104 would be aligned with the end 150 of the outer sheath 108. Also, when the end 158 of the inner sheath 104 is inserted into the outer sheath 108, the indicator 134 of the outer sheath 108 and the indicator 146 of the inner sheath 104 will be aligned when the inner sheath and outer sheath are rotationally aligned. Another variation of the disclosure may include inserting a beveled distal end 158, 162 of the inner sheath 104 into the outer sheath 108 such that one of the beveled distal ends 158, 162 aligns with the non-beveled end 150 of the outer sheath.

It may also be desirable for the user of the sheath set 100 to utilize both ends 158, 162 of the inner sheath 104 during a procedure for separating tissue from a lead in the event that one of the ends 158, 162 becomes dull during the procedure and thereby, potentially becoming less effective in separating tissue. Accordingly, a user may leave the outer sheath 108 in the patient's vasculature while removing the inner sheath 104 completely therefrom and switching the ends 158, 162 of the inner sheath 104 that are inserted into the outer sheath 108 during the procedure by inserting the alternate end back into the outer sheath 108. The indicator of the present disclosure allows the user to do so quickly and effectively because the indicator 112, 116, 138, 146 is the same for both halves of the inner sheath 104, both ends 158, 162 are equally distant from the center of the inner sheath 104, and both ends 158, 162 have the same or similar configuration.

It may also be possible for both halves of the inner sheath 104 to use a single indicator similar to indicator 112, 116 to indicate the alignment of the ends 158, 162 of the inner sheath 104 with the end 154 of the outer sheath 108. For example, if the single indicator is located at the center (with respect to both ends) of the inner sheath 104 and includes two triangular shaped marks spaced apart and facing one another, then a user will be able to align that indicator with the end 150 of the outer sheath 108 and know that either end 158 or end 162 of the inner sheath is located within the end 154 of the outer sheath.

It would be possible to provide for some features of the disclosure without providing others. For example, the inner sheath may only have one beveled end rather than two beveled ends to separate tissue. If so, some of the indicator of the present disclosure may be omitted.

In the appended figures, similar components and/or features may have the same reference label. Further, various components of the same type may be distinguished by following the reference label by a letter that distinguishes among the similar components. If only the first reference label is used in the specification, the description is applicable to any one of the similar components having the same first reference label irrespective of the second reference label.

The present disclosure, in various aspects, embodiments, and/or configurations, includes components, methods, processes, systems and/or apparatus substantially as depicted and described herein, including various aspects, embodiments, configurations embodiments, sub combinations, and/or subsets thereof. Those of skill in the art will understand how to make and use the disclosed aspects, embodiments, and/or configurations after understanding the present disclosure. The present disclosure, in various aspects, embodiments, and/or configurations, includes providing devices and processes in the absence of items not depicted and/or described herein or in various aspects, embodiments, and/or configurations hereof, including in the absence of such items as may have been used in previous devices or processes, e.g., for improving performance, achieving ease and/or reducing cost of implementation.

The foregoing discussion has been presented for purposes of illustration and description. The foregoing is not intended to limit the disclosure to the form or forms disclosed herein. In the foregoing Summary for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method of separating tissue surrounding a lead within a blood vessel, the method comprising the steps of:

inserting a sheath set over a proximal end the lead within the blood vessel, the sheath set comprising:

an outer sheath comprising a proximal end, a beveled distal end, a lumen between the proximal end and the beveled distal end, an exterior surface, and a longitudinal axis, wherein the beveled distal end forms a beveled proximal edge portion with the exterior surface of the outer sheath and a beveled distal edge portion with the exterior surface of the outer sheath, wherein the outer sheath further comprises a rotational position indicator on the exterior surface of the outer sheath and along the longitudinal axis of the outer sheath, wherein the rotational position indicator is longitudinally aligned with the beveled distal edge portion; and an inner sheath comprising a first beveled end, a second beveled end, a center between the first beveled end and the second beveled end, an exterior surface, and a longitudinal axis, the inner sheath located at least partially within the lumen of the outer sheath, wherein the first beveled end forms a first proximal edge portion with the exterior surface of the inner sheath and a first distal edge portion with the exterior surface of the inner sheath, wherein the second beveled end forms a second proximal edge with the exterior surface of the inner sheath and a second distal edge with the exterior surface of the inner sheath, wherein the first proximal edge portion and the second proximal edge are proximate the center relative to the first distal edge portion and the second distal edge, respectively, wherein the inner sheath further comprises a rotational position indicator on the exterior surface of the inner sheath and along the longitudinal axis of the inner sheath, wherein the rotational position indicator is longitudinally aligned with the first distal edge and the second distal edge, and a first indicator on the exterior surface of the inner sheath, wherein the first indicator indicates the first beveled end of the inner sheath is linearly aligned with the beveled distal end of the outer sheath when the first indicator is linearly aligned with the proximal end of the outer sheath, and a second indicator on the exterior surface of the inner sheath, wherein the second indicator indicates the second beveled end of the inner sheath is linearly aligned with the beveled distal end of the outer sheath when the second indicator is linearly aligned with the proximal end of the outer sheath;

aligning the first indicator of the inner sheath with the proximal end of the outer sheath;

aligning the rotational position indicator of the inner sheath with the rotational position indicator of the outer sheath, thereby creating a linearly aligned position for the inner sheath and outer sheath;

advancing the inner sheath and the outer sheath concurrently in the linearly aligned position over the lead in the blood vessel; and further advancing and rotating the inner sheath such that the first beveled end of the inner sheath extends distally of the beveled distal end of the outer sheath.

2. The method of claim 1, further comprising the steps of:
retracting the inner sheath within the outer sheath to the linearly aligned position;

advancing the inner sheath and the outer sheath concurrently in the linearly aligned position over the lead in the blood vessel; and further advancing and rotating the inner sheath such that the first beveled end of the inner sheath extends distally of the beveled distal end of the outer sheath.

3. The method of claim 1, wherein the linearly aligned position is a first linearly aligned position, the rotational position indicator of the inner sheath is a first rotational position indicator, the inner sheath further comprises a second rotational position indicator on the exterior surface of the inner sheath and along the longitudinal axis of the inner sheath, and further comprising the steps of:

removing the inner sheath from the outer sheath;
reinserting the inner sheath into the outer sheath such that the second beveled end of the inner sheath enters the lumen of the outer sheath;

aligning the second indicator of the inner sheath with the proximal end of the outer sheath;

aligning the second rotational position indicator of the inner sheath with the rotational position indicator of the outer sheath, thereby creating a second linearly aligned position for the inner sheath and outer sheath;

advancing the inner sheath and the outer sheath concurrently in the second linearly aligned position over the lead in the blood vessel; and further advancing and rotating the inner sheath such that the second beveled end of the inner sheath extends distally of the beveled distal end of the outer sheath.

4. The method of claim 3, further comprising the steps of:
retracting the inner sheath within the outer sheath to the second linearly aligned position;

advancing the inner sheath and the outer sheath concurrently in the second linearly aligned position over the lead in the blood vessel; and further advancing and rotating the inner sheath such that the second beveled end of the inner sheath extends distally of the beveled distal end of the outer sheath.

5. The method of claim 1, wherein first indicator is at least one pair of indicators, and wherein aligning the first indicator of the inner sheath with the proximal end of the outer sheath comprises aligning the at least one pair of indicators with the proximal end of the outer sheath.

6. The method of claim 5, wherein the at least one pair of indicators comprises two markings comprising a space therebetween, and wherein aligning the at least one pair of indicators with the proximal end of the outer sheath comprises aligning the space with the proximal end of the outer sheath.

7. The method of claim 6, wherein the two markings comprise a shape.

8. The method of claim 7, wherein the two markings are the same shape.

9. The method of claim 8, wherein the two markings are mirror images of the same shape when located on the inner sheath.

10. The method of claim 5, wherein the at least one pair of indicators is longitudinally aligned with the rotational position indicator on the exterior surface of the inner sheath.

11. The method of claim 1, wherein the inner sheath further comprises a circumference, the first indicator comprises one or more sets of indicators, each of the one or more sets of indicators are positioned evenly around the circumference of the inner sheath, and wherein aligning the first indicator of the inner sheath with the proximal end of the outer sheath comprises aligning the one or more sets of indicators with the proximal end of the outer sheath.

12. The method of claim 1, wherein the beveled distal end of the outer sheath is tapered.

13. The method of claim 1, wherein the first beveled end and the second beveled end of the inner sheath are tapered.

* * * * *

UNITED STATES PATENT AND TRADEMARK OFFICE
CERTIFICATE OF CORRECTION

PATENT NO. : 9,675,371 B2
APPLICATION NO. : 14/195692
DATED : June 13, 2017
INVENTOR(S) : Shimon et al.

It is certified that error appears in the above-identified patent and that said Letters Patent is hereby corrected as shown below:

In the Specification

In Column 3, Line 40, delete "therethough." and insert -- therethrough. --, therefor.

In Column 4, Line 39, delete "refracted" and insert -- retracted --, therefor.

In Column 6, Line 27, delete "$X_1$-$X_a$," and insert -- $X_1$-$X_n$, --, therefor.

In Column 8, Line 3, delete "below" and insert -- below. --, therefor.

In Column 8, Line 29, delete "FIG. 4 is" and insert -- FIG. 4 is a --, therefor.

In Column 8, Line 66, delete "therethough" and insert -- therethrough --, therefor.

In Column 12, Line 53, delete "124" 126"," and insert -- 124", 126", --, therefor.

In Column 13, Line 31, delete "120', 124;" and insert -- 120', 124'; --, therefor.

In Column 13, Line 52, delete "wherein the" and insert -- wherein: (1) the --, therefor.

In Column 13, Line 54, delete "126', 130;" and insert -- 126', 130'; --, therefor.

In Column 14, Line 60, delete "as a" and insert -- as --, therefor.

In Column 15, Line 22, delete "124'," and insert -- 124", --, therefor.

Signed and Sealed this
Twenty-ninth Day of August, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,675,371 B2

In Column 17, Line 64, delete "configurations embodiments," and insert -- configurations, --, therefor.

In the Claims

In Column 18, Line 45, in Claim 1, delete "end the" and insert -- end of the --, therefor.